DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MAY 7, 1974

922 O.G. 10

T922,005

FLUORIDE SALTS AS DEHYDROCHLORINATING AGENTS IN THE PREPARATION OF CHLOROPRENE OR 2,3-DICHLORO-1,3-BUTADIENE

Paul Clayton Briggs, Jr., Wilmington, Del., assignor to E. I. du Pont de Nemours and Company, Wilmington, Del.

Filed Nov. 28, 1973, Ser. No. 419,892
Int. Cl. C07c *21/20*
U.S. Cl. 260—655
No Drawing. 13 Pages Specification

Chloroprene is prepared in high yields and without the formation of brine by reacting 3,4-dichloro-1-butene with cesium fluoride, potassium fluoride, an organic quaternary ammonium fluoride, a mixture of cesium fluoride and potassium fluoride, or a mixture of cesium fluoride and sodium fluoride, said reaction being conducted in an aprotic organic solvent.

In the alternative embodiment of this invention 2,3-dichlorobutadiene is similarly prepared from 2,3,4-trichloro-1-butene or meso-1,2,3,4-tetrachlorobutane.

The aprotic solvents useful in this invention are polar organic materials which are liquid under the conditions of the reaction and which form a homogeneous phase with the organic chlorine-containing starting material. The fluorides are only slightly soluble in the solvent, but the solvent should be one which is capable of effectively solvating the cation while leaving the fluoride ion unsolvated in solution. Hydrogen-bonding solvents, such as water and the alcohols, are ineffective.

Suitable solvents include, for example, aliphatic carboxylic acid amides, aliphatic sulfones and sulfoxides, and hexaalkyl phosphoric triamides.

The temperature of the reaction is conveniently from about 25° C. up to about 150° C. In general, the preferred range is about 50° to about 125° C. Temperatures of around 90° to about 110° C. are usually most satisfactory.